US00PP19533P2

(12) United States Plant Patent
van Noort

(10) Patent No.: US PP19,533 P2
(45) Date of Patent: Dec. 2, 2008

(54) ***GERANIUM* PLANT NAMED 'SWEET HEIDY'**

(50) Latin Name: *Geranium wallichianum*
Varietal Denomination: Sweet Heidy

(76) Inventor: Marco van Noort, Wasbecklaan 13, 2361 HG, Warmond (NL)

( * ) Notice: Subject to any disclaimer, the term of this patent is extended or adjusted under 35 U.S.C. 154(b) by 0 days.

(21) Appl. No.: 12/001,156

(22) Filed: Dec. 10, 2007

(51) Int. Cl.
*A01H 5/00* (2006.01)

(52) U.S. Cl. ..... Plt./324
(58) Field of Classification Search ..... Plt./324
See application file for complete search history.

*Primary Examiner*—Kent L Bell
(74) *Attorney, Agent, or Firm*—Penny J. Aguirre

(57) ABSTRACT

A new cultivar of *Geranium wallichianum*, 'Sweet Heidy', characterized by its abundant, tricolor flowers with purple veins; pale violet centers become purple pink in the middle regions and violet-blue near the margin, its long blooming season, its clean foliage with yellow spots, its prostrate spreading growth habit with good performance as a groundcover and its cold hardiness at least to U.S.D.A. Zone 5.

2 Drawing Sheets

Botanical classification: *Geranium wallichianum.*
Cultivar designation: 'Sweet Heidy'.

BACKGROUND OF THE INVENTION

The present invention relates to a new and distinct cultivar of *Geranium* plant, botanically known as *Geranium wallichianum* 'Sweet Heidy' and will be referred to hereafter by its cultivar name, 'Sweet Heidy'.

'Sweet Heidy' was derived from a breeding project in Warmond, The Netherlands. The inventor's goal was to develop new cultivars of *Geranium wallichianum* that are long blooming, free of disease, and exhibit unique flower coloration. 'Sweet Heidy' was selected as a single plant from among the seedlings that resulted from crosses made in 2002 between unnamed pink and blue flowering plants of *Geranium wallichianum.*

Asexual reproduction of the new cultivar was first accomplished by in vitro propagation under the direction of the inventor in Roelofsarensveen, The Netherlands in fall of 2004. Propagation by tissue culture and division has determined that the characteristics of this cultivar are stable and are reproduced true to type in successive generations.

SUMMARY OF THE INVENTION

The following traits have been repeatedly observed and represent the characteristics of 'Sweet Heidy'. These attributes in combination distinguish 'Sweet Heidy' as a new and distinct cultivar of *Geranium.*

1. 'Sweet Heidy' exhibits flowers that are tri-color with purple veins; pale violet centers become purple pink in the middle regions and violet-blue near the margin.
2. 'Sweet Heidy' is long blooming; flowers from May until frost in The Netherlands.
3. 'Sweet Heidy' produces an abundance of flowers continuously through the bloom season.
4. 'Sweet Heidy' has clean green foliage with yellow spots (enlarged vein areas).
5. 'Sweet Heidy' has a prostrate growth habit with suitable use as a groundcover.

6. 'Sweet Heidy' is propagated with ease by division or tissue culture.
7. 'Sweet Heidy' is cold hardy at least to U.S.D.A.9 Zone 5.

The new cultivar, 'Sweet Heidy', is unique from the all other cultivars of *Geranium wallichianum* known to the inventor and is particularly unique for its tri-colored flowers. 'Sweet Heidy', can be compared to *Geranium wallichianum* cultivars 'Buxton's Variety' (not patented) and 'Pink Penny' (U.S. Plant Pat. No. 17,656), both similar in having a long blooming habit. 'Buxton's Variety' differs in particular in having blue flowers while 'Pink Penny' exhibits pink flowers.

BRIEF DESCRIPTION OF THE DRAWING

The accompanying colored photographs illustrate the overall appearance and distinct characteristics of the new *Geranium.* The photographs were taken of three year-old plants of 'Sweet Heidy' as grown outdoors in a two-gallon container in The Netherlands.

The photograph in FIG. 1 is a side view of a plant of 'Sweet Heidy' in bloom in fall.

Figure 1:
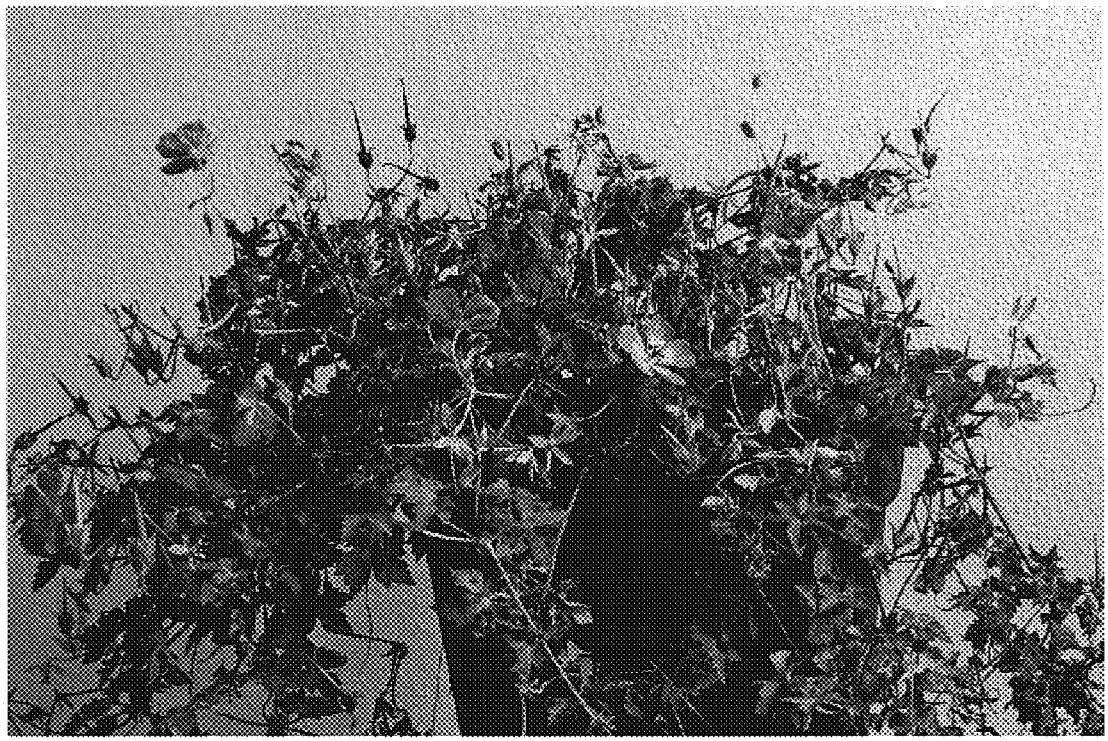
Figure 2:
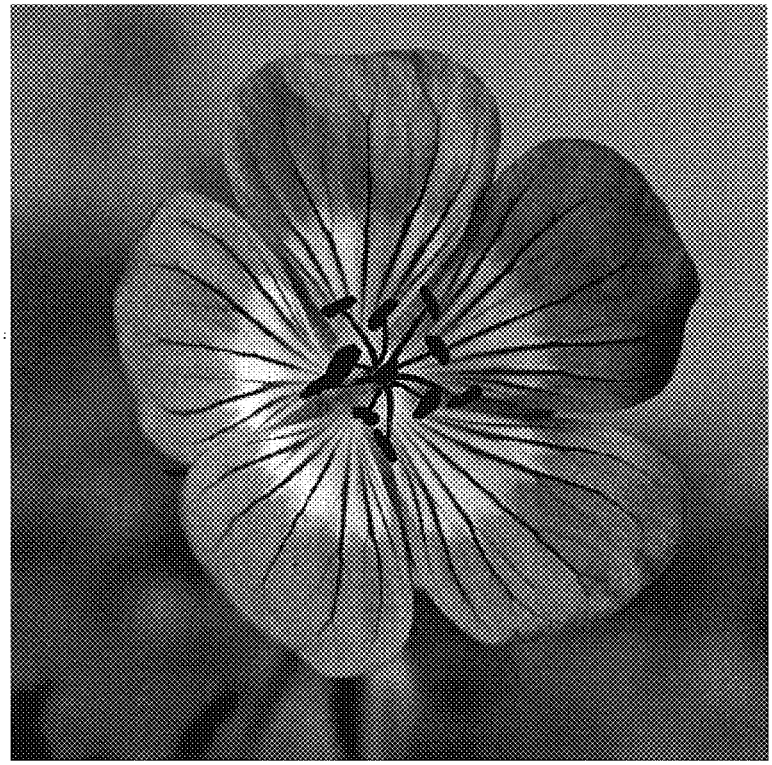
Figure 3:
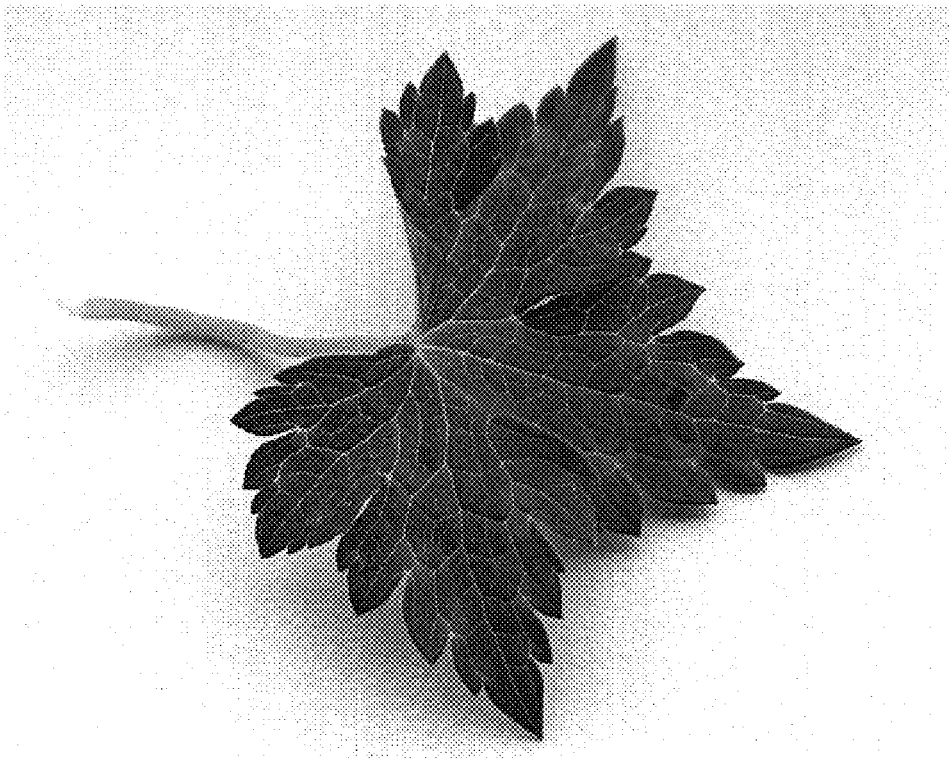

The photograph in FIG. 2 is of a close-up view of a flower of 'Sweet Heidy' and the photograph in FIG. 3 provides a close-up view of a leaf of 'Sweet Heidy'.

The colors in the photographs are as close as possible with the photographic and printing technology utilized. The color values cited in the detailed botanical description accurately describe the colors of the new *Geranium.*

DETAILED BOTANICAL DESCRIPTION OF THE PLANT

The following is a detailed description of 3 year-old, field grown plants of the new cultivar as grown outdoors in Warmond, The Netherlands with average day temperatures of 14° C. to 32° C. and average night temperatures of 7° C. to 15° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General characteristics:

*Blooming period.*—From May until first frost (typically the end of October) in The Netherlands.

*Plant habit.*—Herbaceous perennial with prostrate, spreading growth habit.

*Height and spread.*—Reaches 30 to 35 cm in height and about 45 cm in spread.

*Cold hardiness.*—At least to U.S.D.A. Zone 5.

*Heat tolerance.*—At least tolerant to temperature up to 35° C.

*Diseases and pests.*—No particular resistance or susceptibility in comparison to other cultivars of *Geranium.*

*Root description.*—Fleshy roots extending from stout rootstock.

Growth and propagation:

*Growth rate.*—Moderate to vigorous, about 15 cm per month in spring.

*Propagation.*—Division and In vitro propagation.

*Time required for salable flowering crop.*—About 20 weeks (field grown or 9 cm container).

Stem description:

*Stem size.*—Average of 33.4 cm in length and 3 mm in width, stems are thickened at nodes at a average of 4 mm.

*Stem shape.*—Round.

*Stem color.*—185A.

*Stem surface.*—Slightly glossy with young stems densely covered with soft hairs; average of 1 mm in length, 155C in color.

*Internode length.*—Average of 4.4 cm.

*Branching.*—Freely branched with average of 15 lateral branches.

Foliage description:

*Leaf shape.*—Orbicular.

*Leaf division.*—Simple.

*Leaf base.*—Hastate.

*Leaf apex.*—Acute.

*Leaf venation.*—Palmate, 144A in color on upper surface and 146D on lower surface.

*Leaf margins.*—Palmately cleft, lobes crenate (average:6 teeth per lobe; 3 on each side).

*Leaf attachment.*—Petiolate.

*Leaf arrangement.*—Alternate.

*Leaf surface.*—Pubescent on upper and lower surface with moderately dense coverage of short hairs; average of 1 mm in length, 155C in color.

*Leaf color.*—Young leaves upper surface; 137B, young leaves lower surface; 138B, mature leaves upper surface; 143A to 144A, mature leaves lower surface; 146C to 146D, fall color; typically a blend of 34A and 22A.

*Leaf size.*—Average of 3.7 cm in length and 4.6 cm in width.

*Leaf quantity.*—Average of 7 leaves per lateral branch.

*Petioles.*—Average of 2.6 in length and 1 mm in width, color 145C to 145D with base 184A to 184B, surface is pubescent.

*Stipules.*—1 per leaf, broadly ovate, average of 1.4 cm in length, average of 9 mm in width; 145A to 145B in color, occasionally flushed with 185B.

Flower description:

*Inflorescence type.*—Single, rotate flowers, arranged in pairs.

*Lastingness of flowers.*—About 7 days on the plant, sepals persistent.

*Flower size.*—Average of 1.0 cm in height and 3.7 cm in diameter.

*Flower fragrance.*—None.

*Flower number.*—Average of 14 per inflorescence (7 pairs), about 250 per plant.

*Flower aspect.*—Upright to outward.

*Flower buds.*—Broadly ovate to elliptic in shape, average of 1.1 cm in length and up to 5 mm in width, 143B in color.

*Corolla features.*—Petals are unfused and arranged in a rotate form, slightly cupped.

*Petal number.*—5.

*Petal shape.*—Obcordate.

*Petal color.*—Opening upper surface; outer region N88B to N88C, middle region N78B; center region 84C, veins N79C, opening lower surface; N81C with veins, N79C, fully open upper surface; outer region N78B, center region 87C, veins N79C, fully open lower surface; N81C with veins, N79C, non fading.

*Petal surface.*—Glabrous.

*Petal margins.*—Entire.

*Petal apex.*—Very shallow emarginated.

*Petal size.*—Average of 2.1 cm in length and 1.65 cm in width.

*Calyx form.*—Rotate, becoming campanulate after petal drop.

*Sepals.*—5, elliptic in shape, average of 1.4 cm length and 4.5 mm in width, entire margin, mucronate apex, cuneate base, glabrous and dull surface, color young and mature upper surface 144B, color young and mature lower surface 144A to 144B.

*Peduncles.*—Round in shape, average of 6 cm in length and 1.0 mm in diameter, moderately strong, held at about a 45° angle relative to lateral branch, color 144B with upper surface flushed with 185A, surface is glabrous.

*Pedicels.*—Round in shape, average of 3.6 cm in length and 1 mm in width, moderately strong, held at about a 45° angle relative to peduncle on lateral flowers, color 144B to 144C with upper surface flushed with 197A to 197B.

Reproductive organs:

*Gynoecium.*—1 pistil, about 8 mm in length, 5 stigmas are decurrent and N186C in color, style is about 6 mm in length and N186D in color with base 144B, ovary is 144B to 144C in color and densely covered with very short (about 0.3 mm) hairs N155A in color.

*Androcoecium.*—10 stamens, anthers are dorsifixed, oblong in shape, 2 mm in length, and N186A to 202A in color, filaments are 6 mm in length and N186D in color, with base 150D, pollen is low in quantity and 12B in color.

*Fruit/seeds.*—Fruit comprised of rostrum and 5 mericarps (typical cranesbill form), 250 fruits per plant, 15 per lateral branch, 3.4 cm in length and 6 mm in width, smooth and moderately glossy surface, 200A to 200B in color, seeds: 5 per fruit, 3.5 mm in length, 2 mm in width and 202A in color.

It is claimed:

1. A new and distinct cultivar of *Geranium* plant named 'sweet Heidy' as herein illustrated and described.

* * * * *